United States Patent [19]
Gelotte et al.

[11] 4,310,670
[45] Jan. 12, 1982

[54] LOW-TEMPERATURE, AQUEOUS CONVERSION OF 4-PICOLINE DERIVATIVE TO 5-CYANO-[3,4'-BIPYRIDIN]-6(1H)-ONE

[75] Inventors: Karl O. Gelotte, Nassau; Edward D. Parady, Schodack, both of N.Y.

[73] Assignee: Sterling Drug Inc., New York, N.Y.

[21] Appl. No.: 124,807

[22] Filed: Feb. 26, 1980

[51] Int. Cl.$^3$ .................. C07D 213/22; C07D 213/54
[52] U.S. Cl. .................................... 546/257; 546/258; 546/264
[58] Field of Search ........................ 546/257, 258, 264

[56] References Cited

U.S. PATENT DOCUMENTS 4,004,012  1/1977  Lesher et al. ..................... 424/263
4,107,315  8/1978  Lesher et al. ..................... 424/263
4,137,233  1/1979  Lesher et al. .

OTHER PUBLICATIONS

Arnold, Coll. Czech. Chem. Comm., vol. 28, pp. 863 to 868 (1963).
Nantkanomirski et al, Current Abstracts of Chemistry, vol. 74, Issue 814, item 285573, (1979), (abst. of Polish J. Pharmacol. Pharmacy, vol. 30, pp. 707-712 1978).

*Primary Examiner*—John M. Ford
*Assistant Examiner*—Robert C. Whittenbaugh
*Attorney, Agent, or Firm*—Robert K. Bair; B. Woodrow Wyatt

[57] ABSTRACT

The process which comprises reacting 4-picoline below about 30° C. with at least three mole equivalents of an inorganic acid halide, preferably phosphorus oxychloride, per mole of 4-picoline and excess dimethylformamide, reacting in solution the unisolated resulting N-[3-dimethylamino-2-(4-pyridinyl)-2-propenylidene]-N-methylmethaniminium salt (after adding the reaction mixture to cold water, adjusting the pH to about 8.0 and filtering off the precipitated inorganic cationic salts) with excess α-cyanoacetamide and at least three mole equivalents of base, and then isolating 5-cyano-[3,4'-bipyridin]-6(1H)-one in free base form (after neutralization) or in the form of its inorganic cationic salt. Said 5-cyano-[3,4'-bipyridin]-6(1H)-one is an intermediate for preparing the cardiotonic amrinone.

6 Claims, No Drawings

LOW-TEMPERATURE, AQUEOUS CONVERSION OF 4-PICOLINE DERIVATIVE TO 5-CYANO-[3,4'-BIPYRIDIN]-6(1H)-ONE

CROSS-REFERENCE TO RELATED APPLICATIONS

Copending K. O. Gelotte and C. J. Opalka, Jr. U.S. Patent Application Ser. No. 124,808, filed Feb. 26, 1980, and now U.S. Pat. No. 4,264,609, issued Apr. 28, 1981, discloses and claims the process which comprises the steps of reacting 4-picoline with phosgene and dimethylformamide to produce in almost quantitative yield the novel N-[3-dimethylamino-2-(4-pyridinyl)-2-propenylidene]-N-methylmethaniminium chloride hydrochloride and reacting said salt with Q-$CH_2CONH_2$ and base in anhydrous medium to produce (after neutralization) in high overall yield 3-Q-5-(4-pyridinyl)-2(1H)-pyridinone where Q is cyano or carbamyl; it also discloses and claims each of said steps individually and the N-[3-dimethylamino-2-(4-pyridinyl)-2-propenylidene]-N-methylmethaniminium salt or pharmaceutically-acceptable acid-addition salt thereof as the active component in a cardiotonic composition and a method for increasing cardiac contractility.

Copending C. J. Opalka, Jr. and G. Y. Lesher U.S. Patent Application Ser. No. 60,758, filed July 26, 1979, discloses and claims, inter alia, the process which comprises reacting β-(dimethylamino)-α-(4-pyridinyl)acrolein [alternatively named 3-dimethylamino-2-(4-pyridinyl)-2-propen-1-one] in a lower alkanol to produce 1,2-dihydro-2-oxo-5-(4-pyridinyl)nicotinonitrile, that is, the same as 3-Q-5-(4-pyridinyl)-2(1H)-pyridinone or alternatively named 5-cyano-[3,4'-bipyridin]-6(1H)-one.

BACKGROUND OF THE INVENTION (a) Field of the Invention

This invention relates to an improved method for preparing 5-cyano-[3,4'-bipyridin]-6(1H)-pyridinone directly from 4-picoline.

(b) Description of the Prior Art

Lesher and Opalka U.S. Pat. No. 4,004,012, issued Jan. 18, 1977, shows two methods of preparing 1,2-dihydro-2-oxo-5-(pyridinyl)nicotinonitriles and conversion by hydrolysis to the corresponding nicotinamides, one method of preparing 1,2-dihydro-2-oxo-5-(pyridinyl)nicotinamides, and, in turn, the conversion of the nicotinamides to the corresponding 3-amino compounds. These methods are presented structurally in columns 3 and 4 of U.S. Pat. No. 4,004,012. Two methods are disclosed for preparing 1,2-dihydro-2-oxo-5-(pyridinyl)nicotinonitriles (III in patent), i.e., (1) by reacting α-(pyridinyl)-β-($R_1R_2N$)acrolein (II in patent) with α-cyanoacetamide in the presence of a basic condensing agent, preferably an alkali lower-alkoxide, e.g., sodium methoxide or ethanol; and, (2) by heating α-(pyridinyl)malonaldehyde with α-cyanoacetamide in the presence of a catalytic condensing agent, preferably morpholine or piperidine and/or its acetate. As shown in Example A-1 in the paragraph common to columns 9 and 10 of U.S. Pat. No. 4,004,012, the product in method (1) is collected as its sodium salt, recrystallized and then converted by treatment with hydrochloric acid to 1,2-dihydro-2-oxo-5-(pyridinyl)nicotinonitrile. Also disclosed is a method of preparing 1,2-dihydro-2-oxo-5-(pyridinyl)nicotinamides by reacting α-(pyridinyl)-β-($R_1R_2N$)acrolein with malonamide.

A recently published abstract ["Current Abstracts of Chemistry", Vol. 74, Issued 814, Item 285573, 1979] of a Polish publication [Nantkanomirski and Kaczmarek, Polish J. Pharmacol. Pharmacy 30(5), 707-12 (1978)] shows, inter alia, the reaction of 3-dimethylamino-2-(4-pyridinyl)acrolein [same as β-(dimethylamino)-α-(4-pyridinyl)acrolein] with malononitrile in the presence of sodium methoxide in methanol to produce 2-methoxy-5-(4-pyridinyl)nicotinonitrile.

Arnold [Coll. Czech. Chem. Comm. 28, 863–868 (1963)] shows the preparation of β-dimethylamino-α-(4-pyridinylacrolein by three different methods: (a) formylation of 4-picoline with dimethylformamide and phosphorus oxychloride; (b) formylation of 4-picoline with dimethylformamide and phosgene in chloroform; and, (c) formylation of 4-(2-dimethylaminovinyl)pyridine with dimethylformamide and phosgene in chloroform.

SUMMARY OF THE INVENTION

The invention relates to the process of directly converting 4-picoline to 5-cyano-[3,4'-bipyridin]-6(1H)-one by reacting 4-picoline below about 30° C. with at least three mole equivalents of an inorganic acid halide per mole of 4-picoline and excess dimethylformamide, reacting in solution the unisolated resulting N-[3-dimethylamino-2-(4-pyridinyl)-2-propenylidene]-N-methylmethaniminium salt (after adding the reaction mixture to cold water, adjusting the pH to about 8.0 and filtering off precipitated inorganic cationic salts) with excess α-cyanoacetamide and at least three mole equivalents of base, and then isolating 5-cyano-[3,4'-bipyridin]-6(1H)-one in free base form (after neutralization) or in the form of its inorganic cationic salt.

DETAILED DESCRIPTION INCLUSIVE OF PREFERRED EMBODIMENTS

The invention resides in the process which comprises the steps of reacting 4-picoline below about 30° C., preferably about 20°–25° C., with at least three mole equivalents of an inorganic acid halide, preferably phosphorus oxychloride, per mole of 4-picoline and excess dimethylformamide, adding the reaction mixture to cold water and adjusting the pH to about 8.0 while keeping the temperature between below about 30° C., preferably below 25° C., filtering off precipitated inorganic cationic salts, treating the aqueous filtrate which contains N-[3-dimethylamino-2-(4-pyridinyl)-2-propenylidene]-N-methylmethaniminium salt with an excess of α-cyanoacetamide and at least three mole equivalents of base still keeping the temperature below about 30° C., preferably below 25° C., and then isolating either 5-cyano-[3,4'-bipyridin]-6(1H)-one as its inorganic cationic salt or, after neutralization, in its free base form. The resulting 5-cyano-[3,4'-bipyridin]-6(1H)one is useful as an intermediate in the preparation of amrinone, viz., 3-amino-5-(4-pyridinyl)-2(1H)-pyridinone, alternatively named 5-amino-[3,4'-bipyridin]-6(1H)-one, supra. Preferred embodiments are those where the indicated temperatures are below 25° C., phosphorus oxychloride is used as the inorganic acid halide, and the pH adjustment to about 8.0 is done using aqueous sodium hydroxide solution, thereby resulting in sodium chloride as the inorganic cationic chloride.

The process of the invention has the advantage of not having first to prepare, isolate and purify the heretofore used intermediate for preparing said products, that is, 3-dimethylamino-2-(4-pyridinyl)-2-propen-1-one or β-dimethylamino-α-(4-pyridinyl)acrolein.

The simplified and advantageous utilization in solution of the novel unisolated intermediate, viz., N-[3-dimethylamino-2-(4-pyridinyl)-2-propenylidene]-N-methylmethaniminium salt (e.g., likely a mixture of chloride and dihydrogen phosphate when phosphorus oxychloride is used as the inorganic acid halide) in very good overall yields was realized after isolation of this novel intermediate in acid-addition salt form as N-[3-dimethylamino-2-(4-pyridinyl)-2-propenylidene]-N-methylmethaniminium chloride hydrochloride, which is disclosed and claimed in copending U.S. Patent Application Ser. No. 124,808, filed Feb. 26, 1980 now U.S. Pat. No. 4,264,609, issued Apr. 28, 1981.

The manner of making and using the instant invention will now be generally described so as to enable a person skilled in the art of pharmaceutical chemistry to make and use the same, as follows.

An important feature of the process of the invention is maintaining the temperature below about 30° C., perferably 20°-25° C., through the formation of the inorganic cationic salt of 5-cyano-[3,4'-bipyridin]-6(1H)-one. Although phosphorus oxychloride is the preferred inorganic acid chloride used in the process, other such acid chlorides usable are phosgene, thionyl chloride, sulfuryl chloride, phosphorus trichloride, phosphorus pentachloride, phosphorus tribromide, carbonyl dibromide, thiophosgene, and the like; phosphorus oxychloride was preferred from the standpoint of economy of operation. While aqueous sodium hydroxide solution was preferably used as the base needed for the reaction between N-[3-dimethylamino-2-(4-pyridinyl)-2-propenylidene]-N-methylmethaminium salt and α-cyanoacetamide to produce inorganic cationic salt (sodium salt using NaOH), any other inorganic basic agent capable of producing a pH range of about 10-14, preferably 12-13 can be used, e.g., potassium hydroxide, potassium carbonate, sodium carbonate, and the like. Preferably about a 50% molar excess of α-cyanoacetamide was used to obtain best yields, although a lower molar excess of about 30-35% can be used; of course, a larger excess of α-cyanoacetamide can be used but to no particular advantage. Preferably about six to ten volumes of dimethylformamide per volume of 4-picoline were used; however, the reaction was found to proceed satisfactorily with as little as about five volumes of dimethylformamide per volume of 4-picoline. More dimethylformamide, viz., up to about fifteen to twenty or more volumes of dimethylformamide per volume of 4-picoline can be used but to no particular advantages over a smaller excess.

The product, 5-cyano-[3,4'-bipyridin]-6(1H)-one as its inorganic cationic salt, viz., sodium salt when sodium hydroxide is used as base, is conveniently and preferably isolated from the reaction mixture by filtration. The cationic salt form of the product is readily dissolved in water and in solution is neutralized by addition of acid, preferably acetic acid to a weakly acidic pH, viz., about 5.0 to 6.5, preferably about 6.0 to 6.5.

Isolation of N-[3-dimethylamino-2-(4-pyridinyl)-2-propenylidene]-N-methylmethaniminium salt from the reaction mixture after its addition to cold water, adjusting the pH to 8 and removal of the precipitated inorganic cationic salts is shown hereinbelow.

The following examples will further illustrate the invention without, however, limiting it thereto.

EXAMPLE 1

5-Cyano-[3,4'-bipyridin]-6(1H)-one

To 550 ml. of dimethylformamide cooled in an ice bath was added dropwise with stirring over a two hour period 420 g. (2.75 moles) of phosphorus oxychloride keeping the temperature below 25° C. With continued cooling below 25° C., 85 g. (0.91 mole) of 4-picoline was added dropwise. After addition of 4-picoline had been completed, the cooling bath was removed and the reaction mixture was stirred at ambient temperature overnight. The maximum temperature was 30° C. This solution was added through a dropping funnel to 1.8 liters of ice-cooled water allowing a maximum temperature of 20° C. With continued cooling and stirring, the pH was adjusted to 8.0 by the dropwise addition of 1.10 liters of 35% aqueous sodium hydroxide solution, allowing a maximum temperature of 25° C. When the pH reached 6-7, a heavy but stirrable precipitation of inorganic salts (probably a mixture of sodium chloride and sodium dihydrogen phosphate) ensued. After pH 8 was attained, the reaction mixture was cooled to 10° C. and the solid was collected by filtration. The filter cake of inorganic salts was thoroughly pressed dry and was then washed successively with 200 ml. of ice-cold water and 150 ml. of cold ethanol. The filtrate in a 5 liter flask containing in solution N-[3-dimethylamino-2-(4-pyridinyl)-2-propenylidene]-N-methylmethaniminium salt (probably mixture of chloride and dihydrogen phosphate) was warmed to 15°-20° C. and to the warm solution was added in one portion 132 g. (1.57 moles) of α-cyanoacetamide followed by the addition of 225 ml. of 35% sodium hydroxide over 1 hour. The temperature was not allowed to exceed 25° C. About 20 minutes into the addition, the sodium salt of the product precipitated. After the addition had been completed, the reaction was stirred for another 2 hours, cooled to 10° C., diluted with 1.0 liter of cold ethanol and filtered. The addition of ethanol seemed to enhance the rate of filtration. The aqueous filtrate was set aside before the filter cake was washed free of yellow color with ethanol. The filter cake was then washed with ether to remove some of the ethanol. The off-white sodium salt of the product was dissolved in 2.0 liters of water at 55° C.; the pH of the solution was then adjusted to 6.0 by the dropwise addition of acetic acid and was cooled to 10° C. The precipitated product was collected and the filter cake was washed successively with 100 ml. of cold water, 100 ml. of ethanol and 200 ml. of ether. The light beige powder was dried at 55° C. in vacuo for 20 hours to give 104.0 g. of 5-cyano-[3,4'-bipyridin]-6(1H)-one, m.p. >300° C. The cherry-red aqueous filtrate that had been set aside was adjusted to pH 6 by the dropwise addition of acetic acid. The solution was seeded with the above product, cooled to 10° C. and precipitate collected. The filter cake was washed with 100 ml. of water and dried in vacuo at 55° C. for 20 hours to give another 21.5 g. portion of 5-cyano-[3,4'-bipyridin]-6(1H)-one, m.p. >300° C. The total yield was 125.5 g., amounting to 70.3%.

EXAMPLE 2

N-[3-Dimethylamino-2-(4-pyridinyl)-2-propenylidene]-N-methylmethaniminium Salt In another run following the procedure described in Example 1, the above-entitled intermediate iminium salt was isolated from a sample of the aqueous filtrate of pH 8 after filtering off the inorganic salts (probably a mixture of sodium chloride and sodium dihydrogen phosphate) as follows: A 300 ml. portion of said aqueous filtrate was concentrated in vacuo to dryness. The residue was slurried with six 500 ml. portions of ethyl acetate (decanting the solvent each time) and the remaining residue was stripped on a rotary evaporator at 50° C. to produce, as a viscous material, 8.5 g. of N-[3-dimethylamino-2-(4-pyridinyl)-2-propenylidene]-N-methylmethaniminium salt (probably mostly chloride plus some dihydrogen phosphate), whose NMR is consistent with the assigned structure. This viscous material was placed under high vacuum and was heated on a 50° C. water bath for three hours to remove any remaining water, thereby resulting in 8.0 g. of the material. N-[3-dimethylamino-2-(4-pyridinyl)-2-propenylidene]-N-methylmethaniminium chloride is shown and claimed in copending Application Serial No. 124,808, filed Feb. 26, 1980, now U.S. Pat. No. 4,264,609, issued Apr. 28, 1981.

We claim:

1. The process which comprises the steps of reacting 4-picoline below about 30° C. with at least three mole equivalents per mole of 4-picoline of an inorganic acid halide selected from phosphorus oxychloride, phosgene, thionyl chloride, sulfuryl chloride, phosphorus trichloride, phosphorus pentachloride, phosphorus tribromide, carbonyl dibromide or thiophosgene and about five to twenty volumes of dimethylformamide per volume of 4-picoline, adding the reaction mixture to cold water and adjusting the pH to about 8.0 while keeping the temperature below about 30° C., filtering off the precipitated inorganic cationic salt, treating the aqueous filtrate which contains N-[3-dimethylamino-2-(4-pyridinyl)-2-propenylidene]-N-methylmethaniminium salt with at least about 30–35% molar excess of α-cyanoacetamide and at least three mole equivalents of base still keeping the temperature below about 30° C., and then isolating either 5-cyano-[3,4'-bipyridin]-6(1H)-one as its inorganic cationic salt or, after neutralization, in its free base form.

2. The process according to claim 1 where phosphorus oxychloride is used as the inorganic acid halide.

3. The process according to claim 1 wherein sodium hydroxide is used as the base.

4. The process according to claim 1 where the indicated temperature range in each instance is below 25° C.

5. The process according to claim 1 where about six to ten volumes of dimethylformamide per volume of 4-picoline are used.

6. The process according to claim 1 where about a 50% molar excess of α-cyanoacetamide is used.

* * * * *